United States Patent [19]
Allen

[11] Patent Number: 4,810,244
[45] Date of Patent: Mar. 7, 1989

[54] TROCAR ASSEMBLY FOR DRAWING FLUIDS FROM A BODY PART

[75] Inventor: Thomas C. Allen, Summerville, N.Y.

[73] Assignee: Mark L. Anderson, Elmwood, Wis.

[21] Appl. No.: 134,465

[22] Filed: Dec. 17, 1987

[51] Int. Cl.⁴ .............................................. A61M 5/14
[52] U.S. Cl. ...................................... 604/44; 604/164;
604/283
[58] Field of Search .................... 604/44, 43, 164, 35,
604/165–169, 283, 284

[56] References Cited
U.S. PATENT DOCUMENTS

| | | | |
|---|---|---|---|
| 3,312,220 | 4/1967 | Eisenberg | 604/164 |
| 4,004,588 | 1/1977 | Alexander | 604/43 |
| 4,016,879 | 4/1977 | Mellor | 604/44 |
| 4,037,599 | 7/1977 | Ravlerson | 604/44 |
| 4,468,216 | 8/1984 | Muto | 604/43 |
| 4,531,935 | 7/1985 | Berryessa | 604/44 |

Primary Examiner—Stephen C. Pellegrino
Attorney, Agent, or Firm—Edward H. Loveman

[57] ABSTRACT

This surgical trocar assembly has the needle of a stylet removably disposed inside a first cannula which is inside a second cannula in a concentric array. The needle has a sharp point to pierce a body part to be drained of fluids. A first fitting on the first cannula has a first nipple to engage an aspiration tube when the needle is removed. The fitting has a tenon to engage in a tubular member of a Y-shaped joint structure. The tubular member has a lateral second nipple to engage an end of a wash fluid feed tube. A second fitting on the second cannula engages on the tubular member so that wash water passes through the tubular member between the first and second cannulas. The first cannula has a tapered sharp open end to enter the body part for aspirating fluids therefrom. The second cannula has a tapered end to engage the outside of the first cannula near its tapered open end, and further has lateral openings to discharge wash fluid from the second cannula to the body part.

12 Claims, 3 Drawing Sheets

TROCAR ASSEMBLY FOR DRAWING FLUIDS FROM A BODY PART

BACKGROUND OF THE INVENTION

1. Field of the Invention

This invention relates to the art of surgical trocars and more particularly concerns an improved trocar assembly having plural cannulas for draining fluid from a body part, for repeatedly washing the body part and for draining the wash fluid after each wash.

2. Description of the Prior Art

Surgical trocars (or "trochars") generally employ a sharp pointed stylet needle for piercing a body part to be drained of fluid. The stylet needle is often inserted in a cannula through which the fluid can be aspirated after the stylet is removed or even while the stylet needle is still in place if it is loosely fitted in the cannula. This type of conventional trocar assembly of stylet and cannula is satisfactory for most macroscopic surgical purposes, but it presents a number of difficulties and disadvantages when it is required to remove microscopically small eggs or oocytes from a follicle or follicles in a human ovary, as is required in performing in vitro fertilization procedures. The principal disadvantage encountered with the prior trocars is that it is difficult or impossible to wash a follicle while under microscopic observation to insure that any oocyte present is removed. If the washing fluid is fed through the cannula to the drainage site in the ovary after the original follicular fluid has been aspirated, any oocyte which may have remained in the cannula may be washed back into the ovary and there lost. Furthermore, use of the prior trocars unduly prolongs the operative procedure where the pierced follicle must be washed several times, four for example; so that a patient must be kept under anesthesia a longer time than is desirable.

SUMMARY OF THE INVENTION

It is a principal object of the present invention to overcome or avoid the above mentioned, and other difficulties and disadvantages encountered with prior surgical trocars used in performing extraction of oocytes from follicles in human ovaries, or in other drainage procedures performed under microscope observation. According to the present invention, there is provided a trocar assembly which comprises inner and outer cannulas, one cannula being inserted coaxially in the other. The outer ends of the two cannulas terminate in fittings which engage in opposite ends of a tubular portion of a Y-shaped joint structure. The joint has a lateral branch nipple which opens into the outer cannula for feeding wash fluid to the oocyte extraction site, via lateral openings in the outer cannula. The inner cannula serves to drain by aspiration the original follicular fluid as well as the wash fluid subsequently and repeatedly supplied via the outer cannula. The inner cannula is sharp pointed and tapered to penetrate the follicle being drained. If desired a sharp pointed stylet or needle may be inserted through the inner cannula for initially piercing the ovary and follicle. This stylet will be removed and replaced by an aspiration tube connected to a nipple on the fitting at the outer end of the inner cannula, to aspirate the follicular fluids.

These and other objects and many of the attendant advantages of this invention will be readily appreciated as the same becomes better understood by reference to the following detailed description when considered in connection with the accompanying drawings in which:

DESCRIPTION OF THE PREFERRED EMBODIMENTS

Figure 1:
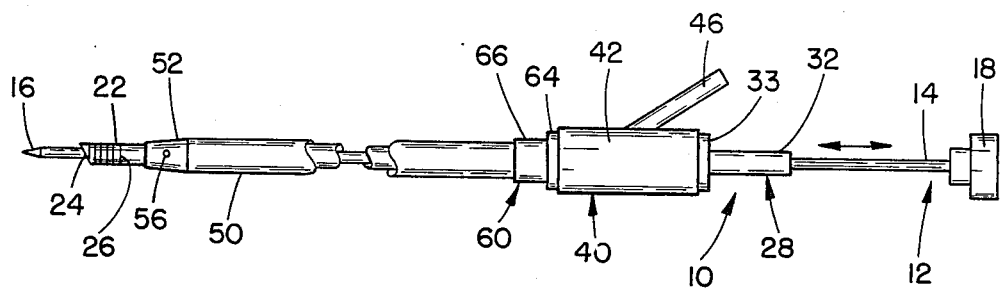
FIG. 1 is a side elevational view of a trocar assembly embodying the invention, parts of inner and outer cannulas being broken away.
Figure 7:
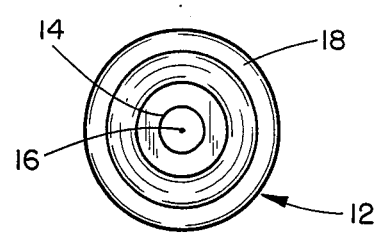
FIG. 7 is an end elevational view taken along line 7—7 of FIG. 6.
Figure 8:
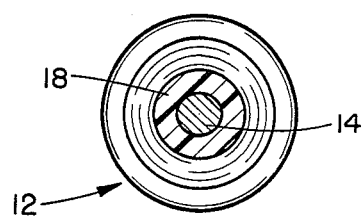
FIG. 8 is a cross sectional view taken along line 8—8 of FIG. 6.
Figure 6:
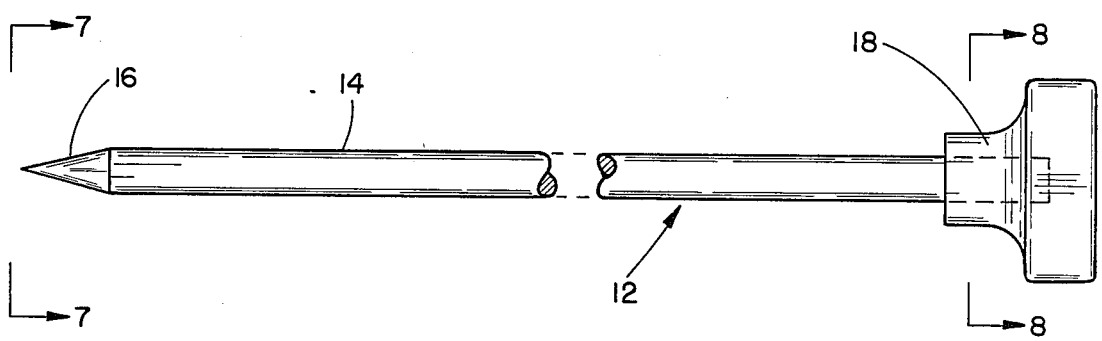
FIG. 6 is an enlarged side elevational view of the stylet per se, part being broken away.
Figure 9:
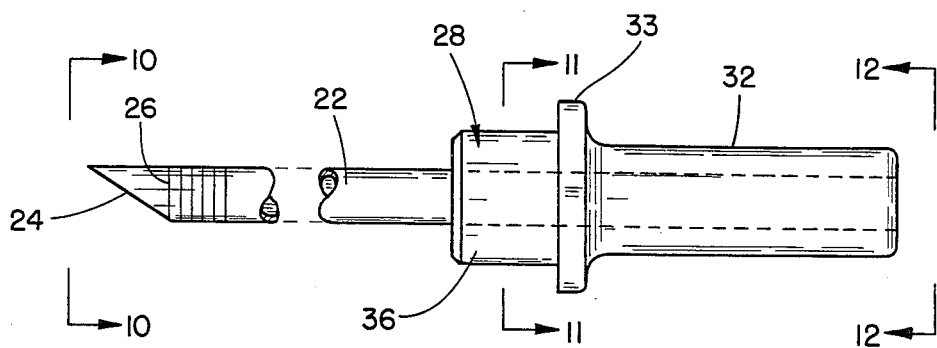
FIG. 9 is an enlarged side elevational view of the inner cannula of the trocar assembly, part being broken away.
Figure 10:
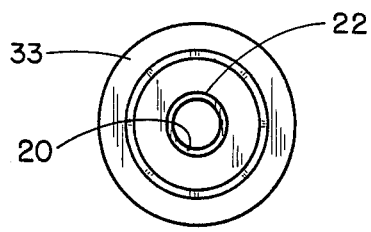
FIG. 10 is an end elevational view taken along line 10—10 of FIG. 9.
Figure 11:
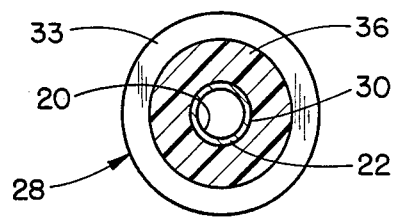
FIG. 11 is a cross sectional view taken along line 11—11 of FIG. 9.
Figure 12:
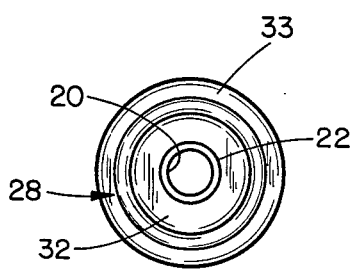
FIG. 12 is an end elevational view taken along line 12—12 of FIG. 9.

Referring now to the drawings wherein like reference characters designate like or corresponding parts throughout, there is illustrated in FIG. 1 a trocar assembly generally designated by reference numeral 10 comprising a stylet 12 including a long needle 14 terminating in a sharp point 16 at one end, as best shown in FIGS. 6–8. The other end of the needle 14 is secured in a knob 18 which facilitates manipulating the needle 14 to pierce an ovary and follicle. The needle 14 extends axially through a passage 20 in the first or inner cannula 22; see FIG. 10. One end 24 of the cannula 22 is out at an acute angle to define a rather sharp point which if desired may have a multiplicity of short cuts or grooves 26 spaced laterally apart around the cannula 22. The grooves 26 serve to reflect ultrasonic images of the cannula 22, thereby permitting the surgeon to properly position the needle 14. At the other end of the cannula 22 is a generally cylindrical fitting 28 having an axial bore 30 through which the cannula 22 extends; see FIG. 11. The fitting 28 has a nipple 32 engages an aspiration tube 34 (shown in FIG. 2). Adjacent the flange 33 is a short cylindrical tenon 36 which fits snugly and axially into the outer end of a Y-shaped joint structure 40.

The joint structure 40, shown in FIGS. 1-5, has a tubular or cylindrical body member 42 with an axial passage 44 therethrough. One end 44' of the passage 44 receives the tenon 36 of the fitting 28 indicated by dotted lines in FIG. 5. The joint 40 has a nipple 46 integral with the tubular member 42. The nipple 46 extends laterally of the member 42 and also extends axially at an acute angle to the axis of the member 42, with a passage 45 opening into the passage 44. A wash fluid tube 48 for feeding wash water or other fluid to the follicular site being drained, may be attached to the nipple 46; see FIG. 2.

Figure 2:
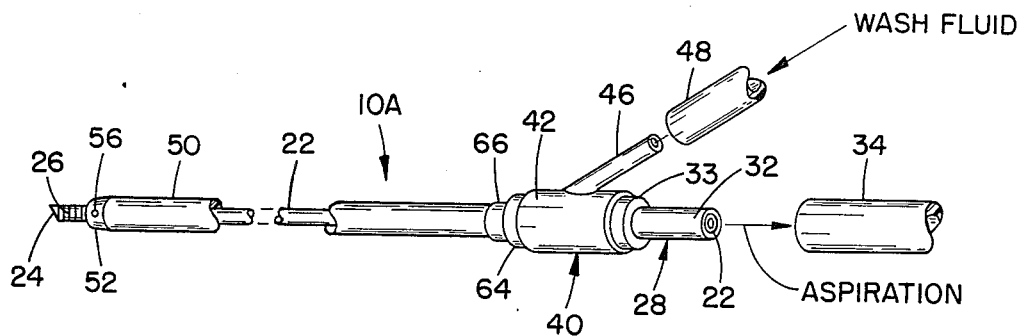
FIG. 2 is an oblique view of the trocar assembly, with stylet removed, aspiration and wash fluid tubes detached, and parts, of the cannulas broken away.
Figure 3:
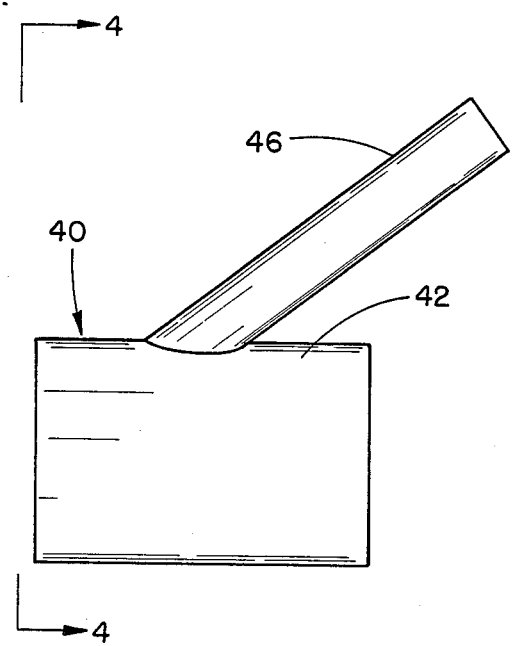
FIG. 3 is a side elevational view on a large scale of the Y-joint structure per se.
Figure 4:
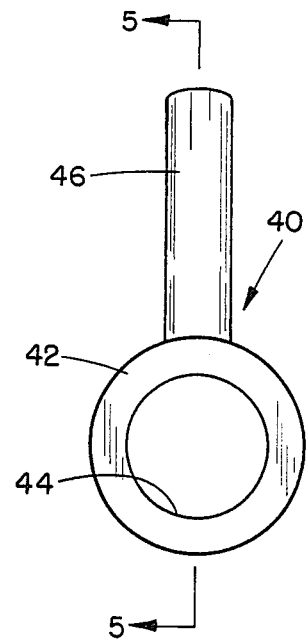
FIG. 4 is an end elevational view taken along line 4—4 of FIG. 3.
Figure 5:
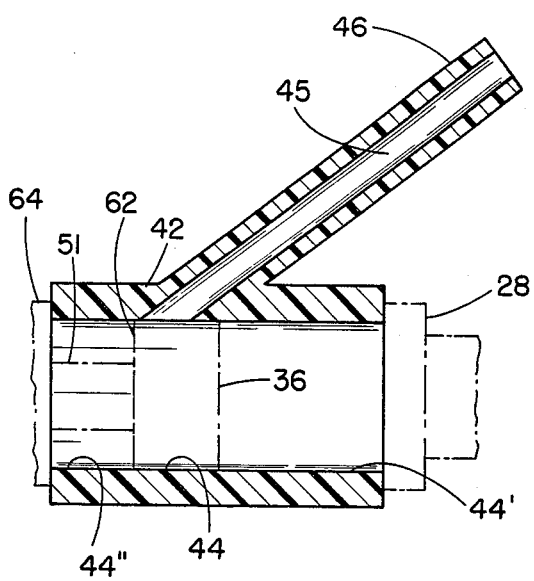
FIG. 5 is a longitudinal, central sectional view taken along line 5—5 of FIG. 4.
Figure 13:
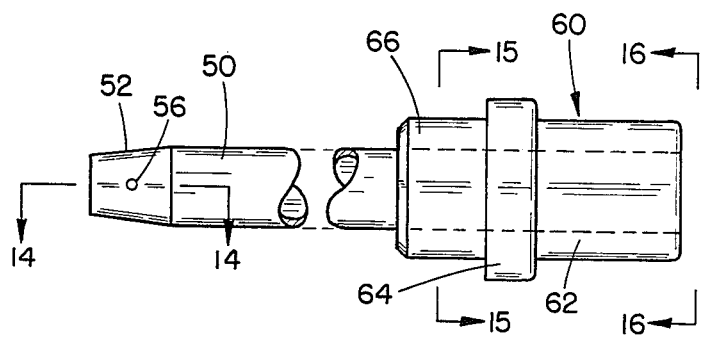
FIG. 13 is an enlarged side elevational view of the outer cannula, part being broken away.
Figure 14:
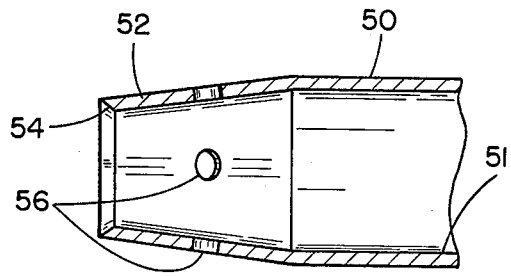
FIG. 14 is a fragmentary axial sectional view taken along line 14—14 of FIG. 13.
Figure 15:
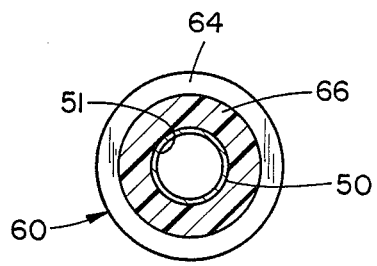
FIG. 15 is a cross sectional view taken along line 15—15 of FIG. 13.
Figure 16:
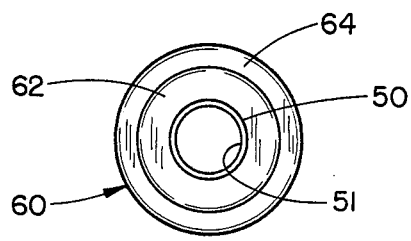
FIG. 16 is an end elevational view taken along line 16—16 of FIG. 13.

The assembly 10 further comprises a second or outer cannula 50 which is coaxial with the inner cannula 22 as shown in FIGS. 1, 2. Cannula 50 has an axial passage 51, and a conically tapered end portion 52 formed with a rolled or curved edge 54; see FIGS. 13 and 14. The cannula end portion 52 snugly engages around the inner cannula 22 just inwardly of the obliquely tapered sharp tip 24. A plurality of holes or apertures 56, spaced apart circumferentially of the cannula tip or end 52, discharge wash fluid laterally from the passage 51, to the follicular site to be washed. At its other end, the cannula 50 is secured to a fitting 60 shown in FIGS. 1, 2, 13, 15, and 16. The fitting 60 has a tenon 62 at its outer end which fits snugly into an end 44'' of the joint passage 44 of the cylindrical member 42 as indicated by dotted lines in FIG. 5. The fitting 60 has an annular ridge or flange 64 which serves as a stop or abutment against the adjacent end of the joint member 42. The fitting 60 has an inner cylindrical end portion 66 which extends from the flange 64 and may be manually gripped for inserting a tenon 62 into the passage 44 in the joint member 42. It will be noted from FIG. 5 that the passage 45 in the joint member 42 opens into the passage 44 and the passage 51 communicates with the passage 44, so that wash fluid supplied via the tube 48 and the nipple 46 readily passes through the passage 51. It will also be understood that the cannula 22 passes through passages 44 and 51 in the member 42 and the cannula 50, and that the passage 20 is isolated from passages 44 and 51.

The fittings 28 and 60 and the joint 40 are preferably made of a lightweight, chemically stable plastic material. The cannulas 22, 50 and the needle 14 may be made of flexible surgical steel, plastic, or other suitable materials. These latter parts may be made as long as necessary, up to fifteen inches or more, for example, to reach a follicular site in an ovary, or any body part to be drained, washed, and drained again.

In use and operation of the assembly 10 shown in FIG. 1, the surgeon performing the procedure will insert the end of the entire coaxial assembly of needle 14, cannula 22, and cannula 50 into a body cavity to pierce the body part to be drained. The pointed end 16 of needle 14 pierces a follicle in an ovary, when a follicular drainage procedure is being performed while being observed under a microscope, to locate one or more oocytes. Then the needle 14 is entirely withdrawn and the aspiration tube 34 is attached to the nipple 32 of the joint 28, as shown in assembly 10A of FIG. 2. Then the follicular fluid is aspirated via the cannula 22. The wash fluid feed tube 48 can then be attached to nipple 46 of the Y-shaped joint structure 40, if it has not been previously so attached. The wash fluid will then be fed via the tube 48. The nipple 46, the passage 44 in the cylindrical member 42, and the passage 51 in the cannula 50, to exit via one or more apertures 56 in the cannula tip 52. The follicular wash fluid will be aspirated via the tube 34, the nipple 32 of the fitting 28, and the cannula 22. A plurality of washes and drainages may be made of the follicular site in rapid succession, and then the assembly 10A may be withdrawn. In some operations, it may not be necessary to use the stylet 12, since the sharp point 24 of the cannula 22 may be fine enough to pierce the body part to be drained, washed, and drained again.

In a practical embodiment of the assembly 10, the needle 12 may be nine to fourteen inches long or more, and approximately 0.05 inches in diameter. The cannula 22 may be approximately eight to thirteen inches long, i.e. shorter than the needle 12. The cannula 22 may be approximately 0.07 inches in diameter and the passage 21 may have a diameter of about 0.06 inches. The cannula 50 will be shorter than the cannula 22, with a length ranging from approximately 7.7 to 12.5 inches, and an external diameter of 0.110 inches. The internal diameter of the cannula 50 may be about 0.09 inches, so that the passage 51 is larger in diameter than that of the cannula 22 by approximately 0.02 inches to provide a channel for the wash fluid around the cannula 22 inside the cannula 50. The tenons 36 and 62 may each be about 0.19 inches in diameter and 0.125 inches long to fit snugly in the passage 44 of the tubular member 42. The passage 44 may be more than 0.25 inches long to provide communication between the passage 44 and the passage 51.

It should be understood that the foregoing relates to only a limited number of preferred embodiments of the invention, which have been by way of example only, and that it is intended to cover all changes and modifications of the example of the invention herein chosen for the purpose of the disclosure, which do not constitute departures from the spirit and scope of the inventions.

What is claimed is:

1. A trocar assembly for draining fluids from a body part, comprising:
    a first cannula having an axial first passage and being open at opposite ends for aspirating fluids from said body part, one of said ends being adapted for insertion into said body part for aspirating said fluids therefrom;
    a first fitting at the other end of said cannula for engaging an external aspiration means;
    a joint structure comprising a member with a second passage therein;
    fluid passing means on said member communicating with said second passage and adapted for engaging an external source of wash fluid to pass said wash fluid into said second passage, said fitting engaging on said member with said first passage isolated from said second passage;
    a second cannula having an axial third passage for passing said wash fluid therethrough, said second cannula having one end disposed adjacent to said one end of said first cannula for feeding said wash fluid to said body part, said second cannula having an open other end; and
    a second fitting on said other end of said second cannula engaging on said member with said third passage communicating with said second passage to receive said wash fluid therefrom; whereby said wash fluid may pass from said external source thereof passage to said body part, and whereby said wash fluid may be aspirated from said body part through said first passage in said first cannula.

2. A trocar assembly as defined in claim 1, wherein said first cannula extends axially through said second and third passages inside said member and said second cannula respectively, and wherein said first passage is open at said first fitting.

3. A trocar assembly as defined in claim 2, further comprising a stylet having a needle longer than said first cannula and having a sharp point, said needle being removably insertable through said first passage until said sharp point projects from said one end of said first cannula to pierce said body part while said needle and said first and second cannulas are disposed in coaxial array.

4. A trocar assembly as defined in claim 3, wherein said one end of said first cannula is tapered to remain in said body part when said needle is withdrawn from said first passage.

5. A trocar assembly as defined in claim 4, wherein said one end of said second cannula is tapered and frictionally engages said first cannula near said one end of said first cannula and further comprising at least one lateral aperture in said second cannula near said one end thereof to discharge said wash fluid from said third passage to said body part.

6. A trocar assembly as defined in claim 1, wherein said member is tubular and is open at opposite ends of said second passage, said first fitting having a first tenon engaging at one end of said second passages, said second fitting having a second tenon engaging in the other end of said second passage, while said first cannula inside said second cannula.

7. A trocar assembly as defined in claim 6, wherein said fluid passing means is a nipple extending laterally to said member so that said joint structure is generally Y-shaped, said nipple being adapted to engage an end of an external wash fluid feed tube.

8. A trocar assembly as defined in claim 7, wherein said first fitting has another nipple thereon for engaging an end of an external aspirating tube.

9. A trocar assembly as defined in claim 8, wherein said first cannula extends axially through said second and third passages inside said member and said second cannula respectively and wherein said first passage is open at said other nipple of said first fitting.

10. A trocar assembly as defined in claim 9, further comprising a stylet having a needle longer than said first cannula and having a sharp point, said needle having removably insertable through said first passage until said sharp point projects from said one end of said first cannula to pierce said body part while said needle and said first and second cannulas are disposed in coaxial array.

11. A trocar assembly as defined in claim 10, wherein said one end of said first cannula is tapered to remain in said body part when said needle is withdrawn from said first passage.

12. A trocar assembly as defined in claim 11, wherein said one end of said second cannula is tapered and frictionally engages said first cannula near said one end of said first cannula and further comprising at least one lateral aperture in said second cannula near said one end thereof to discharge said wash fluid from said third passage to said body part.

* * * * *

REEXAMINATION CERTIFICATE (3549th)
United States Patent [19]
Allen

[11] B1 4,810,244
[45] Certificate Issued Jun. 16, 1998

[54] TROCAR ASSEMBLY FOR DRAWING FLUIDS FROM A BODY PART

[75] Inventor: Thomas C. Allen, 431 Lister Rd., Landrum, S.C. 29356

[73] Assignee: Thomas C. Allen, Landrum, S.C.

Reexamination Request:
No. 90/004,239, May 8, 1996

Reexamination Certificate for:
Patent No.: 4,810,244
Issued: Mar. 7, 1989
Appl. No.: 134,465
Filed: Dec. 17, 1987

[51] Int. Cl.$^6$ .................. A61M 3/00; A61M 5/178; A61M 25/00
[52] U.S. Cl. .................. 604/44; 604/164; 604/283
[58] Field of Search .................. 604/43, 44, 35, 604/164–169, 283, 284, 264, 272, 274, 275

[56] References Cited

U.S. PATENT DOCUMENTS 4,096,860  6/1978  McLaughlin.

4,299,217  11/1981  Sagae et al..

OTHER PUBLICATIONS

Trounson et al. eds. *In Vitro Fertilization and Embryo Transfer*, pp. 191–193 (1984).

*Primary Examiner*—Ronald K. Stright, Jr.

[57] ABSTRACT

This surgical trocar assembly has the needle of a stylet removably disposed inside a first cannula which is inside a second cannula in a concentric array. The needle has a sharp point to pierce a body part to be drained of fluids. A first fitting on the first cannula has a first nipple to engage an aspiration tube when the needle is removed. The fitting has a tenon to engage in a tubular member of a Y-shaped joint structure. The tubular member has a lateral second nipple to engage an end of a wash fluid feed tube. A second fitting on the second cannula engages on the tubular member so that wash water passes through the tubular member between the first and second cannulas. The first cannula has a tapered sharp open end to enter the body part for aspirating fluids therefrom. The second cannula has a tapered end to engage the outside of the first cannula near its tapered open end, and further has lateral openings to discharge wash fluid from the second cannula to the body part.

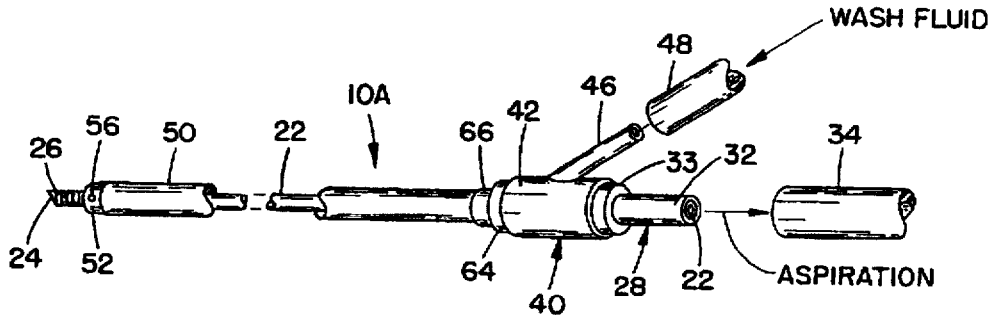

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

Claims 1, 5 and 6 are determined to be patentable as amended.

Claims 2-4 and 7-12, dependent on an amended claim, are determined to be patentable.

New claims 13, 14 and 15 are added and determined to be patentable.

1. A trocar assembly for draining fluids from a body part, comprising:

a first cannula having an axial first passage and being open at opposite ends for aspirating fluids from said body part, one of said ends being adapted for insertion into said body part for aspirating said fluids therefrom *and having means for reflecting ultrasound to identify the location of said trocar assembly within said body part*;

a first fitting at the other end of said cannula for engaging an external aspiration means;

a joint structure comprising a member with a second passage therein;

fluid passing means on said member communicating with said second passage and adapted for engaging an external source of wash fluid to pass said wash fluid into said second passage, said fitting engaging on said member with said first passage isolated from said second passage;

a second cannula having an axial third passage for passing said wash fluid therethrough, said second cannula having one end disposed adjacent to said one end of said first cannula for feeding said wash fluid to said body part, said second cannula having an open other end; and a second fitting on said other end of said second cannula engaging on said member with said third passage communicating with said second passage to receive said wash fluid therefrom; whereby said wash fluid may pass from said external source thereof passage to said body part, and whereby said wash fluid may be aspirated from said body part through said first passage in said first cannula.

5. A trocar assembly [as defined in claim 4,] *for draining fluids from a body part, comprising:*

*a first cannula having an axial first passage and being open at opposite ends for aspirating fluids from said body part, one of said ends being adapted for insertion into said body part for aspirating said fluids therefrom;*

*a first fitting at the other end of said cannula for engaging an external aspiration means;*

*a joint structure comprising a member with a second passage therein;*

*fluid passing means on said member communicating with said second passage and adapted for engaging an external source of wash fluid to pass said wash fluid into said second passage, said fitting engaging on said member with said first passage isolated from said second passage;*

*a second cannula having an axial third passage for passing said wash fluid therethrough, said second cannula having one end disposed adjacent to said one end of said first cannula for feeding said wash fluid to said body part, said second cannula having an open other end;*

*a second fitting on said other end of said second cannula engaging on said member with said third passage communicating with said second passage to receive said wash fluid therefrom; whereby said wash fluid may pass from said external source thereof passage to said body part, and whereby said wash fluid may be aspirated from said body part through said first passage in said first cannula; and*

*a stylet having a needle longer than said first cannula and having a sharp point, said needle being removably insertable through said first passage until said sharp point projects from said one end of said first cannula to pierce said body part while said needle and said first and second cannulas are disposed in coaxial array* wherein *said first cannula extends axially through said second and third passages inside said member and said second cannula respectively, and wherein said first passage is open at said first fitting;* wherein *said one end of said first cannula is tapered to remain in said body part when said needle is withdrawn from said first passage;* wherein *said one end of said second cannula is tapered and frictionally engages said first cannula near said one end of said first cannula and further comprising at least one lateral aperture in said second cannula near said one end thereof to discharge said wash fluid from said third passage to said body part.*

6. A trocar assembly [as defined in claim 1,] *for draining fluids from a body part, comprising:*

*a first cannula having an axial first passage and being open at opposite ends for aspirating fluids from said body part, one of said ends being adapted for insertion into said body part for aspirating said fluids therefrom;*

*a first fitting at the other end of said cannula for engaging an external aspiration means;*

*a joint structure comprising a member with a second passage therein;*

*fluid passing means on said member communicating with said second passage and adapted for engaging an external source of wash fluid to pass said wash fluid into said second passage, said fitting engaging on said member with said first passage isolated from said second passage;*

*a second cannula having an axial third passage for passing said wash fluid therethrough, said second cannula having one end disposed adjacent to said one end of said first cannula for feeding said wash fluid to said body part, said second cannula having an open other end; and*

*a second fitting on said other end of said second cannula engaging on said member with said third passage communicating with said second passage to receive said wash fluid therefrom; whereby said wash fluid may* pass from said external source thereof passage to said body part, and whereby said wash fluid may be aspirated from said body part through said first passage in said first cannula;

wherein said member is tubular and is open at opposite ends of said second passage, said first fitting having a first tenon engaging at one end of said second passages, said second fitting having a second tenon engaging in the other end of said second passage, while said first cannula inside said second cannula.

13. The trocar assembly as defined in claim 1, wherein said first cannula and said axial first passage are straight.

14. The trocar assembly as defined in claim 1, wherein said first cannula is located at least partially within said second cannula.

15. The trocar assembly as defined in claim 1, wherein said means for reflecting ultrasound comprises at least one of a cut and a groove.

* * * * *